United States Patent
Pesnell et al.

(10) Patent No.: US 9,056,092 B2
(45) Date of Patent: Jun. 16, 2015

(54) HEMOSTATIC BIOABSORBABLE DEVICE WITH POLYETHYLENE GLYCOL BINDER

(75) Inventors: Aaron D. Pesnell, Belle Mead, NJ (US); Gerard Llanos, Stewartsville, NJ (US)

(73) Assignee: Ethicon, Inc., Somerville, NJ (US)

( * ) Notice: Subject to any disclaimer, the term of this patent is extended or adjusted under 35 U.S.C. 154(b) by 288 days.

(21) Appl. No.: 13/324,115

(22) Filed: Dec. 13, 2011

(65) Prior Publication Data

US 2013/0149343 A1  Jun. 13, 2013

Related U.S. Application Data

(60) Provisional application No. 61/566,051, filed on Dec. 2, 2011.

(51) Int. Cl.

| | |
|---|---|
| *A61L 15/28* | (2006.01) |
| *A61K 38/36* | (2006.01) |
| *A61K 38/48* | (2006.01) |
| *A61L 15/26* | (2006.01) |
| *A61L 15/32* | (2006.01) |
| *A61L 15/64* | (2006.01) |

(52) U.S. Cl.
CPC ........... *A61K 38/363* (2013.01); *A61K 38/4833* (2013.01); *A61L 15/26* (2013.01); *A61L 15/32* (2013.01); *A61L 15/64* (2013.01); *A61L 2300/418* (2013.01); *A61L 2400/04* (2013.01); *A61L 15/28* (2013.01)

(58) Field of Classification Search
CPC ......... A61L 15/26; A61L 15/28; A61L 15/32; A61L 15/64; A61L 2300/418; A61L 2400/04; C08L 1/28; C08L 67/04; A61K 2300/00; A61K 38/363; A61K 38/4833
See application file for complete search history.

(56) References Cited

U.S. PATENT DOCUMENTS

| | | | |
|---|---|---|---|
| 6,056,970 A * | 5/2000 | Greenawalt et al. .......... 424/426 |
| 6,596,304 B1 * | 7/2003 | Bayon et al. ................. 424/444 |
| 6,706,690 B2 | 3/2004 | Reich et al. | |
| 7,320,962 B2 | 1/2008 | Reich et al. | |
| 7,666,803 B2 | 2/2010 | Shetty et al. | |
| 2006/0088589 A1 | 4/2006 | Gorman et al. | |
| 2007/0160653 A1 | 7/2007 | Fischer et al. | |
| 2009/0053288 A1 | 2/2009 | Eskridge, Jr. | |
| 2009/0246238 A1 | 10/2009 | Gorman et al. | |
| 2011/0071499 A1 | 3/2011 | Hakimimehr et al. | |

FOREIGN PATENT DOCUMENTS

| | | |
|---|---|---|
| EP | 2052746 | 4/2009 |
| WO | WO 97/28832 | 8/1997 |
| WO | WO 2008/053475 A1 * | 5/2008 ............. A61K 9/14 |

* cited by examiner

*Primary Examiner* — Aradhana Sasan
(74) *Attorney, Agent, or Firm* — David R. Crichton; Leo B. Kriksunov

(57) ABSTRACT

A hemostatic pad comprising a bioabsorbable scaffolding material; a lyophilized thrombin powder, a lyophilized fibrinogen powder, and a meltable binder powder, with all powders disposed on the bioabsorbable scaffolding material. A meltable binder such as PEG bonds the lyophilized thrombin powder and the lyophilized fibrinogen powder to the bioabsorbable scaffolding material for improved friability, wettability and performance in a use, such as for hemostatic treatment or sealing at a wound site.

12 Claims, 3 Drawing Sheets

HEMOSTATIC BIOABSORBABLE DEVICE WITH POLYETHYLENE GLYCOL BINDER

FIELD OF THE INVENTION

The present invention relates generally to agents and devices for promoting hemostasis and tissue sealing and, more particularly, to hemostatic pads comprising bioabsorbable scaffolds carrying lyophilized hemostasis promoting proteins, such as fibrinogen and thrombin.

BACKGROUND

Blood is a liquid tissue that includes red cells, white cells, corpuscles, and platelets dispersed in a liquid phase. The liquid phase is plasma, which includes acids, lipids, dissolved electrolytes, and proteins. One particular protein suspended in the liquid phase is fibrinogen. When bleeding occurs, the fibrinogen reacts with water and thrombin (an enzyme) to form fibrin, which is insoluble in blood and polymerizes to form clots.

In a wide variety of circumstances, animals, including humans, can suffer from bleeding due to wounds or during surgical procedures. In some circumstances, the bleeding is relatively minor, and normal blood clotting functions in addition to the application of simple first aid are all that is required. In other circumstances substantial bleeding can occur. These situations usually require specialized equipment and materials as well as personnel trained to administer appropriate aid.

In an effort to address the above-described problems, materials have been developed for controlling excessive bleeding. Topical bioabsorbable hemostats (TAHs) are widely used in surgical applications. TAHs encompass products based on various woven or non-woven fabrics or sponges, typically made of at least partially resorbable materials, ranging from natural to synthetic polymers and combinations thereof, including lactide-glycolide based co-polymers such as Polyglactin 910, oxidized cellulose (OC), oxidized regenerated cellulose (ORC), gelatin, collagen, chitin, chitosan, etc. To improve the hemostatic performance, scaffolds based on the above materials can be combined with biologically-derived clotting factors, such as thrombin and/or fibrinogen.

A number of hemostatic formulations currently available on the market or in development utilize lyophilized fibrinogen, frequently in combination with lyophilized thrombin, with hemostatic formulations applied in the form of dry powder, semi-liquid paste, liquid formulation, or optionally disposed on a supporting scaffold such as bioabsorbable fabric scaffold.

For the hemostatic patches or pads containing lyophilized thrombin and fibrinogen on bioabsorbable scaffolds, there is a need to improve device performance and properties, with particularly needed enhancements related to improved wettability of the pads, leading to faster reconstitution of the lyophilized proteins, and faster hemostasis; reduced friability, i.e. reduced shedding of active powders during handling and/or cutting of the pads; and improved tissue adhesion and wound sealing properties.

U.S. Pat. No. 7,320,962 entitled "Hemoactive compositions and methods for their manufacture and use", discloses a dried hemoactive material for inhibiting bleeding or delivering an agent, comprising: a cross-linked biologically compatible polymer which forms a hydrogel when exposed to blood; and a non-cross-linked biologically compatible polymer which solubilizes when exposed to blood: wherein the cross-linked polymer is dispersed in a dried matrix of the non-cross-linked polymer. The reference further discloses a plasticizer present in at least the non-cross-linked polymer and teaches that the plasticizer is selected from the group consisting of polyethylene glycol, sorbitol, and glycerol.

U.S. Pat. No. 6,706,690 entitled "Hemoactive compositions and methods for their manufacture and use", discloses a dried material which forms a hydrogel when exposed to blood, said material comprising: a cross-linked biologically compatible polymer which forms a hydrogel when exposed to blood; a non-cross-linked biologically compatible polymer which dissolves when exposed to blood; a plasticizer present in the non-cross-linked biologically compatible polymer; and wherein the cross-linked polymer is dispersed in a dried matrix of the non-cross-linked polymer, wherein the non-cross-linked biologically compatible polymer dissolves in 15 minutes or less when exposed to blood. The reference further discloses a plasticizer present in the non-cross-linked polymer at from 1 weight % to 20 weight % of the material, and teaches that the plasticizer is selected from the group consisting of polyethylene glycol, sorbitol, and glycerol.

U.S. Patent Application No. 2011/0071499A1 entitled "FREE-STANDING BIODEGRADABLE PATCH", discloses a device comprising: a film comprising a mixture of solid fibrinogen and solid thrombin, wherein the film is free-standing and is configured to form a fibrin patch upon exposure to moisture and further teaches that the film further comprises a plasticizer. It further discloses the device wherein the film comprises about 5 to about 30 weight percent polyethylene glycol.

U.S. Patent Application No. 2009/0053288A1 entitled "Hemostatic woven fabric" discloses a woven fabric having a modified crowsfoot weave pattern, further comprising a hemostatic agent. The reference further discloses the woven fabric further comprising a preservative selected from the group consisting of glycerol, propanediol, polyoxyethylene glycol (PEG), trehalose, and combinations thereof.

U.S. Patent Application No. 2007/0160653A1 entitled "Hemostatic textile" discloses a hemostatic textile, comprising: a material comprising glass fibers and one or more secondary fibers selected from the group consisting of silk fibers; polyester fibers; nylon fibers; ceramic fibers; raw or regenerated bamboo fibers; cotton fibers; rayon fibers; linen fibers; lactide and/or glycolide polymers; lactide/glycolide copolymers; thrombin or a fraction containing thrombin; and one or more hemostatic agents selected from the group consisting of RL platelets, RL blood cells; fibrin, and fibrinogen; said hemostatic textile capable of activating hemostatic systems in the body when applied to a wound. The reference further discloses the hemostatic textile further comprising a preservative selected from the group consisting of glycerol, propanediol, polyoxyethylene glycol (PEG), trehalose, and combinations thereof.

PCT Patent Publication No. WO 1997028832 A1 entitled "COMPOSITION FOR SEALING WOUNDS" discloses a hemostatic bandage contains powdered fibrinogen and thrombin adhered to a fibrous matrix with a viscous, nonaqueous adhesive such as a viscous polysaccharide, glycol, or petroleum jelly. The nonaqueous adhesive does not allow a hydrolytic reaction to occur between the fibrinogen and thrombin until the bandage is moistened by a body fluid, such as blood and teaches that the bandage can be prepared and stored for prolonged periods while retaining hemostatic activity. The reference further discloses a composition for decreasing a flow of blood from a wound, comprising: a carrier; coagulation constituents adhered to the carrier by an adhesive selected from the group consisting of water at a pH at which thrombin and fibrinogen do not interact to form fibrin, and a viscous nonaqueous biocompatible adhesive, the coagulation constituents being present in a therapeutically sufficient amount to clot and decrease the flow of blood from the wound when the composition contacts body fluids that activate clotting. The reference further discloses the composition wherein the adhesive is a nonaqueous liquid at 20° C. that adheres the coagulation constituents to the carrier. The reference further discloses the composition, wherein the nonaqueous adhesive is selected from the group consisting of propylene glycol, glycerol, petroleum jelly and polyethylene glycol.

The reference further teaches a hemostatic wound dressing, comprising: a fibrous matrix suitable for placement as a pad applied over or inserted into an open, bleeding wound; a mixture of intermingled particles of powdered coagulation factors present on the surface of the matrix, the particles being in sufficiently close contact with each other to form a clot when exposed to an aqueous medium at a physiological pH, the particles being adhered to the matrix by a viscous nonaqueous adhesive, having a viscosity of at least 100 centipoise at 20° C., that inhibits a clotting reaction between the intermingled particles until the particles are exposed to an aqueous medium at physiological pH.

The reference further discloses a hemostatic wound dressing, comprising: a fibrous matrix suitable for placement as a pad applied over or inserted into an open, bleeding wound; a mixture of intermingled particles of powdered coagulation factors present throughout the matrix, in sufficiently close contact to form a clot when exposed to an aqueous medium at a physiological pH, the particles being adhered to the matrix by a viscous nonaqueous adhesive that inhibits a clotting reaction between the intermingled particles until the particles are exposed to an aqueous medium at physiological pH, wherein the adhesive is selected from the group consisting of a polysaccharide, polyethylene glycol, propylene glycol, glycerol, and petroleum jelly, which adhesive has been applied to the matrix in a liquid form comprising less than 3% by weight water.

SUMMARY OF THE INVENTION

Briefly, in one embodiment, the present invention is directed towards and a hemostatic pad having improved friability and wettability and a method of manufacturing such hemostatic pad, said hemostatic pad comprising: a bioabsorbable or bioresorbable scaffolding material; a lyophilized thrombin powder, a lyophilized fibrinogen powder, and a polyethylene glycol powder (PEG), all disposed on the bioabsorbable scaffolding material; wherein the PEG powder bonds the lyophilized thrombin powder and the lyophilized fibrinogen powder to the bioabsorbable scaffolding material but does not fully envelope the lyophilized thrombin powder and/or the lyophilized fibrinogen powder particles. Bioabsorbable and bioresorbable are used interchangeably herein to mean materials that can be broken down by the body and that do not require mechanical removal.

In one embodiment, the present invention is directed towards a method of manufacturing a hemostatic pad, comprising the steps of (a) forming a suspension of a lyophilized thrombin powder, a lyophilized fibrinogen powder, and a polyethylene glycol powder in a non-aqueous fluid; (b) coating the suspension onto a scaffold made of a bioresorbable material; (c) allowing the fluid to evaporate, with the scaffold carrying a portion of the thrombin powder, the fibrinogen powder, and the polyethylene glycol powder; (d) heating the scaffold to a temperature exceeding the polyethylene glycol melting point but not exceeding temperature for appreciable denaturation of thrombin and fibrinogen; (e) cooling the scaffold to ambient temperature to form the hemostatic pad.

In one embodiment, the present invention is directed towards a method of providing a hemostatic treatment or tissue sealing to a wound site, comprising the steps of: (a) forming the hemostatic pad as described above and (b) applying the hemostatic pad to the wound site.

DETAILED DESCRIPTION OF THE INVENTION

Figure 1:
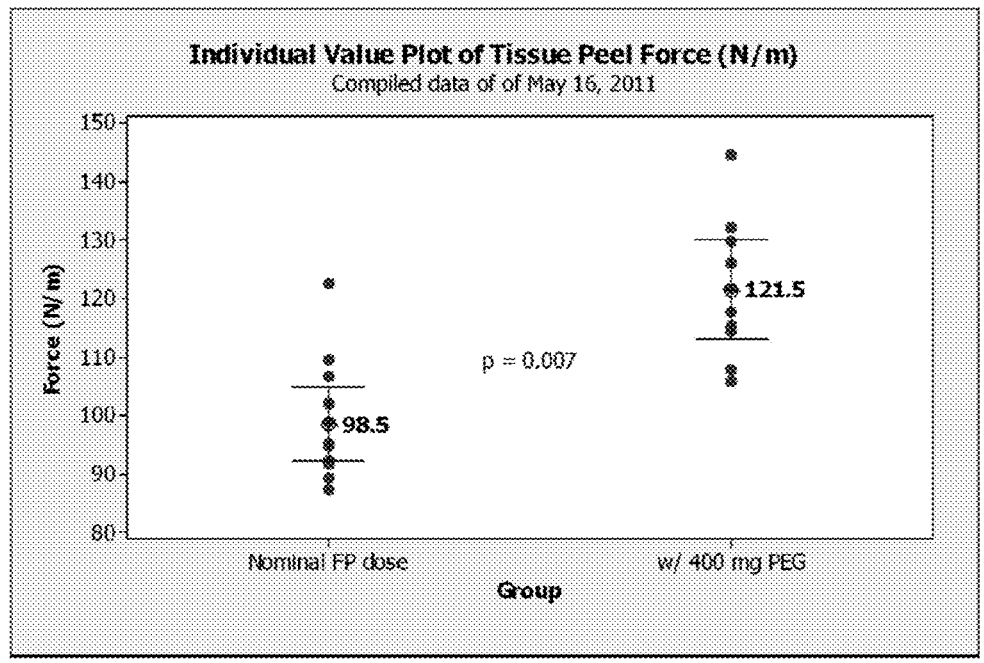
FIG. 1 shows tissue peel test data and effects of PEG additive.

Briefly, in one embodiment, the present invention is directed towards a hemostatic pad having improved friability and wettability and a method of manufacturing such hemostatic pad, said hemostatic pad comprising: a bioabsorbable scaffolding material; a lyophilized thrombin powder, a lyophilized fibrinogen powder, and a polyethylene glycol powder, all disposed on the bioabsorbable scaffolding material; wherein the PEG powder bonds the lyophilized thrombin powder and the lyophilized fibrinogen powder to the bioabsorbable scaffolding material but does not fully envelope the lyophilized thrombin and the lyophilized fibrinogen powder particles.

According to one embodiment of the present invention, meltable PEG, optionally in the presence of CMC, is used to create stronger adhesion of lyophilized proteins to the bioabsorbable scaffolding material and better wettability/adhesiveness of the resulting hemostatic pad, whereby melted and re-solidified PEG binds proximal particles or powders and scaffold fibers, but does not fully coat or envelope the powders/particles so as to allow moisture to access and readily activate these biologic agents in a surgical setting. This results in a low cost solution to friability reduction along with improved tissue adhesion and sealing.

In one embodiment, the present invention is directed to a hemostatic or tissue sealing material or pad. In another embodiment, the present invention also relates to a method of providing a hemostatic treatment or tissue sealing to a wound site, comprising the steps of: (a) forming the hemostatic or tissue sealing material or pad as described above, and (b) applying the hemostatic or tissue sealing material to the wound site.

Hemostatic Pad Containing Lyophilized Fibrinogen and Thrombin

According to an embodiment, the present invention is directed to a hemostatic pad containing lyophilized hemostasis-promoting agents, optionally lyophilized, on a bioabsorbable scaffold or matrix. Preferred hemostatic scaffolds are natural or genetically engineered bioabsorbable polymers or synthetic bioabsorbable polymers, or mixtures thereof.

Examples of natural or genetically engineered bioabsorbable polymers are proteins, polysaccharides and combinations thereof. Polysaccharides include, without limitation, cellulose, oxidized cellulose, oxidized regenerated cellulose (ORC), alkyl cellulose, e.g. methylcellulose, alkylhydroxyalkyl cellulose, hydroxyalkyl cellulose, cellulose sulfate, salts of carboxymethyl cellulose, carboxymethyl cellulose, carboxyethyl cellulose, chitin, carboxymethyl chitin, hyaluronic acid, salts of hyaluronic acid, alginate, alginic acid, propylene glycol alginate, glycogen, dextran, dextran sulfate, curdlan, pectin, pullulan, xanthan, chondroitin, chondroitin sulfates, carboxymethyl dextran, carboxymethyl chitosan, chitosan, starch, amylose, amylopectin, poly-N-glucosamine, polymannuronic acid, polyglucuronic acid, polyguluronic acid, and derivatives of any of the above.

Examples of synthetic bioabsorbable polymers are polyester polymers, copolymers, and/or combinations thereof. The polyesters are typically synthesized in a ring opening polymerization of monomers including, but not limited to, lactic acid, lactide (including L-, D-, meso and D, L mixtures), glycolic acid, glycolide, ε-caprolactone, p-dioxanone (1,4-dioxan-2-one), and trimethylene carbonate (1,3-dioxan-2-one).

Hemostasis promoting agents include proteins, prothrombin, thrombin, fibrinogen, fibrin, fibronectin, heparinase, Factor X/Xa, Factor VII/VIIa, Factor IX/IXa, Factor XI/XIa, Factor XII/XIIa, tissue factor, batroxobin, ancrod, ecarin, von Willebrand Factor, collagen, elastin, albumin, gelatin, platelet surface glycoproteins, vasopressin, vasopressin analogs, epinephrine, selectin, procoagulant venom, plasminogen activator inhibitor, platelet activating agents, synthetic peptides having hemostatic activity, and/or combinations thereof.

A hemostatic pad containing lyophilized thrombin and fibrinogen on bioabsorbable scaffold utilized in the experimental testing of the present invention is referred to as enhanced hemostatic biologics-containing pad and consists of a composite matrix of Polyglactin 910 (PG910) fibers that have been needle punched into an ORC backing layer. The PG910 side of the matrix is coated with human fibrinogen and thrombin powders in a dry, unreacted state. When the enhanced hemostatic biologics-containing pad is applied to a bleeding site, the proteins are readily hydrated (within seconds) resulting in the conversion of fibrinogen to fibrin forming a fibrin clot. Fibrin formation on the tissue surface promotes hemostasis and adhesion to the tissue. Importantly, the proteins remain in an unreacted state prior to application to the tissue. Premature conversion of fibrinogen to fibrin (pre-activation) due to the exposure of water during production or storage could have a negative impact on performance and stability.

U.S. Pat. No. 7,666,803 to Shetty, et al. entitled "Reinforced bioabsorbable multilayered fabric for use in medical devices" is incorporated herein by reference in its entirety for all purposes and teaches a multilayered fabric comprising a first bioabsorbable nonwoven fabric and a second bioabsorbable woven or knitted fabric comprising oxidized polysaccharides.

United States Patent Application publication 2009/0246238 A1 by Gorman et al., entitled "REINFORCED BIOABSORBABLE MULTILAYERED HEMOSTATIC WOUND DRESSING" is incorporated herein by reference in its entirety for all purposes and teaches a method for making a multilayered wound dressing having a first bioabsorbable nonwoven fabric, one or more second bioabsorbable woven or knitted fabric, thrombin and/or fibrinogen, comprising the steps of: (a) crimping bioabsorbable polymer fibers or yarns in the range of about 10 to 30 crimps per inch; (b) cutting the crimped fibers or yarns to a staple length between about 0.1 and 2.5 inch; (c) carding the staple to form the first bioabsorbable nonwoven fabric while controlling the humidity to about 20 to 60%, at a room temperature of about 15 to 24° C.; (d) attaching the first bioabsorbable nonwoven fabric to the second bioabsorbable woven or knitted fabric; (e) applying thrombin and/or fibrinogen to the first bioabsorbable nonwoven fabric. The reference further discloses a method for making a wound dressing comprising bioabsorbable nonwoven fabric, thrombin and/or fibrinogen, comprising the steps of: (a) suspending the thrombin and/or fibrinogen in a perfluorinated hydrocarbon to form a suspension; and (b) applying the suspension to the bioabsorbable nonwoven fabric.

European Patent Publication EP 2,052,746 A2, entitled "Method for making an bioabsorbable hemostat", by Gorman et al., is incorporated herein by reference in its entirety for all purposes, and discloses a method of making a wound dressing, characterized in that said method comprises: suspending thrombin and/or fibrinogen powder in a perfluorinated hydrocarbon carrier fluid in which they are not soluble, and applying the resulting suspension to a first bioabsorbable nonwoven fabric.

Published United States Patent Application 2006/0088589 A1, entitled Method for making an absorbable hemostat, Gorman et al., is incorporated herein by reference in its entirety for all purposes, and discloses a method of making a wound dressing, characterized in that said method comprises: suspending thrombin and/or fibrinogen powder in a perfluorinated hydrocarbon carrier fluid in which they are not soluble, and applying the resulting suspension to a first absorbable nonwoven fabric.

Hemostatic biologics-containing pads made as described in the above references were utilized in the experiments carried out in the practice of the present invention.

The matrix component of hemostatic biologics-containing pad consists of a knitted ORC backing layer under a layer of Polyglactin 910 (PG910) non-woven fibers. During the matrix manufacturing process, the PG910 fibers are carded into a batt and needle-punched to the ORC backing to produce the matrix for the enhanced hemostatic biologics-containing pad.

The biological components of the hemostatic biologics-containing pad are preferably the lyophilized forms of the human fibrinogen and human thrombin drug substances. The fibrinogen and thrombin substances can alternatively be obtained from non-human animal sources or derived synthetically in known fashion. The composition of the hemostatic biologics-containing pad used in the experiments will be clear from the data presented below. In addition to the amounts of active powders as described below, the inventive hemostatic biologics-containing pads optionally also were coated with varying amounts of PEG3000 and CMC, as described later in the text. The biological components of the fibrinogen-containing pad are preferably lyophilized forms of the human fibrinogen and human thrombin. They respectively contain the biologically active ingredients, fibrinogen and thrombin, and other excipients. The compositions of the human fibrinogen and human thrombin as applied to the fibrinogen-containing pad are 2-20 mg/cm2 fibrinogen and 1-150 IU/cm2 thrombin. The composition of the scaffold or matrix component of the hemostatic biologics-containing pad was about 5-30 mg/cm$^2$ of ORC (as a backing layer); and 5-30 mg/cm$^2$ of PG910 (as a carrier layer), with the total matrix having weight of about 10-60 mg/cm$^2$.

The compositions of the human fibrinogen and human thrombin as applied to the hemostatic biologics-containing pad was about 2-20 mg/cm2 fibrinogen and 1-150 IU/cm2 thrombin, with other excipients present, such as calcium chloride, optional arginine, glycine, albumin, mannitol, buffer salts and other optional protein components conventionally found in blood plasma derived products.

Example 1

Manufacturing of Hemostatic Biologics-Containing Pad Test Samples

Following procedures similar to ones described in the above referenced United States Patent Application publication 2009/0246238 A1 and European Patent Publication EP 2,052,746 A2, Poly(glycolide-co-lactide) (PGLA, 90/10 mol/mol) was melt-spun into fiber. A 80 denier multifilament yarn was consolidated into a 800 denier consolidated yarn. The consolidated yarn was crimped at approximately 110° C. The crimped yarn was cut into staple having a length of about 1.25" in length 20 grams of the crimped staple was accurately weighed and laid out uniformly on the feed conveyor belt of a multi-roller carding machine. The environmental conditions (temp: 21° C./55% RH) were controlled. The staple was then carded to create a nonwoven batt. The batt was removed from the pick-up roller and cut into 4 equal parts. These were re-fed into the carder perpendicular to the collection direction. After this second pass, the batt was weighed (19.8 g: 99% fabric yield) and then compacted into a felt. The compact felt was precisely laid onto an ORC fabric and firmly attached via needle-punching. The multilayered fabric was trimmed and scoured in 3 discrete isopropyl alcohol baths to remove spin finish and any machine oils. The scoured multilayered fabric was dried in an oven at 70° C. for 30 minutes, cooled and weighed.

The scoured multilayered fabric was then cut into 4×4 inch pieces. 1.70 grams of BAC-2 (Omrix Biopharmaceuticals, Inc.) having a specific activity (by Clauss) 0.3 g/g and 0.30 g of thrombin-containing powder (also from Omrix Biopharmaceuticals, Inc.) and optionally 0.40 g of polyethylene glycol (PEG) and optionally 0.30 g of carboxymethylcellulose (CMC) powder were mixed thoroughly with about 14 milliliters of non-aqueous fluid, hydrofluoroether HFE-7000. The slurry was poured into a tray with a well slightly larger than 4×4 inches, to accommodate the fabric. The fabric was then dip-coated in the slurry to substantially deposit the powders on the fabric. The resulting multilayered hemostatic pad was air dried for at least 15 minutes.

The test samples containing PEG, with some samples also optionally containing CMC, were then subjected to heat treatment at the temperature exceeding the melting point of the PEG. The samples were positioned in a standard vacuum oven having a temperature setting of 65-70° C. and heated for approximately 15 minutes. The lyophilized thrombin and fibrinogen particles coated on the bioabsorbable scaffold, and optionally the CMC particles, are thus fused to the scaffold by heating to a temperature exceeding PEG melting point. The test samples were then allowed to cool to room temperature.

The hydrofluoroether (HFE) fluid was 3M Novec™ Engineered Fluid HFE-7000, 1-methoxyheptafluoropropane that is commercially available from 3M Corporation. HFE-7000 is an inert, nonflammable, low boiling point fluid. HFE-7000 is used as an inert delivery vehicle for the thrombin and fibrinogen and optionally PEG and/or CMC powder during manufacture, and is substantially completely removed by evaporation during the manufacturing process. Any other inert, nonflammable, low boiling point non-aqueous fluid could be utilized as an inert delivery vehicle for the thrombin and fibrinogen and optionally PEG and/or CMC powder during manufacture of the inventive hemostatic pads.

Any meltable biologically compatible and bioabsorbable powder can be used in practicing the present invention, provided that it is solid at ambient temperature and has a melting temperature below the temperature of appreciable denaturation of the lyophilized proteins. The preferred binder is PEG having average molecular weight of 1000 to 20,000 Daltons, and more preferably PEG 3000 to 8000. In the current example PEG 3000 was used, obtained from Fluka, with melting point of about 56-59° C. and a number average particle size of 45 microns. In a preferred embodiment, the binder particles have at least 95% by number of the particles with a particle size in the range of about 25-60 microns, more preferably in the range of 35-55 microns.

CMC (30,000 PA Clear and Stable) was obtained from Dow Wolff Cellulosics and had an average particle size of 20 microns.

BAC-2 (biologically active component 2) is a blood-derived product that contains primarily fibrinogen, the rest including albumin, buffer salts and other protein components conventionally found in blood plasma derived products.

Three types of hemostatic biologics-containing pads samples were manufactured according to the process described above and experimentally tested:
  a) Hemostatic biologics-containing pads containing fibrinogen and thrombin;
  b) Hemostatic biologics-containing pads containing fibrinogen, thrombin, and PEG;
  c) Hemostatic biologics-containing pads containing fibrinogen, thrombin, PEG, and CMC.

The hemostatic biologics-containing pads containing small amounts of PEG unexpectedly exhibited improved properties, including improved peel strength, friability and wettability. The functional outcome of these improvements is enhanced sealing and tissue adhesion properties, along with reduced friability of actives.

Example 2

Tissue Peel Testing

The following variable levels of concentrations of active components were utilized:
BAC-2 fibrinogen-containing powder: 5.0 and 6.7 mg/cm$^2$ of fibrinogen or 1.27 grams and 1.7 grams of fibrinogen-containing BAC-2 powder as per 4×4" Hemostatic biologics-containing pad sample.
Thrombin containing powder: 300 mg of thrombin-containing powder per 4×4" Hemostatic biologics-containing pad sample.
PEG: 0; 100, 400 mg per 4"×4" hemostatic biologics-containing pad sample.
CMC: 0; 300 mg per 4"×4" hemostatic biologics-containing pad sample.

The tissue peel test was performed as follows. A test sample of a hemostatic biologics-containing pad having the width of 0.75 inches and about 4 inches long was placed on moist bovine corium tissue. A compression weight applying 180 mm Hg pressure was immediately placed on top of the hemostatic biologics-containing pad test sample, and three minutes were allowed for incubation and adherence to tissue. Following incubation the weight was removed and the hemostatic biologics-containing pad sample was clamped to a crosshead and then peeled away from the corium tissue at 90 degrees and the peel force was measured using a tensiometer.

Referring now to Table 1 and to FIG. 1, tissue peel test results are presented.

TABLE 1

Tissue Peel Test results

| Pad sample No. | BAC2 (g) | Thrombin (mg) | PEG3000 (mg) | CMC 30k (mg) | Mean Peel Strength (N/m) |
|---|---|---|---|---|---|
| 9, 14 (n = 6) | 1.700 | 300 | 0 | 0 | 94.80 |
| 10 | 1.700 | 300 | 100 | 0 | 106.87 |
| 11 | 1.700 | 300 | 100 | 300 | 122.72 |

TABLE 1-continued

Tissue Peel Test results

| Pad sample No. | BAC2 (g) | Thrombin (mg) | PEG3000 (mg) | CMC 30k (mg) | Mean Peel Strength (N/m) |
|---|---|---|---|---|---|
| 12 | 1.700 | 300 | 400 | 0 | 120.76 |
| 13 | 1.700 | 300 | 400 | 300 | 126.00 |
| 15 | 1.270 | 300 | 100 | 0 | 85.93 |
| 17 | 1.270 | 300 | 400 | 0 | 95.04 |
| 20 | 1.270 | 300 | 100 | 300 | 73.00 |
| 24 | 1.270 | 300 | 400 | 300 | 118.68 |

Analysis of the data presented in Table 1 indicates that presence of PEG3000 in the amount ranging from 100 to 400 mg significantly improves tissue peel strength of the hemostatic biologics-containing pad, with more PEG resulting in higher peel strength. Further analysis of the data indicates that similarly, with an exception of one test, presence of CMC 30 k in the amount of 300 mg improves the tissue peel strength of the hemostatic biologics-containing pad.

Referring now to FIG. 1, individual data points as well as average values for tissue peel test showing specifically the effects of 400 mg of PEG on tissue peel are presented. The chart presents the data for hemostatic biologics-containing pad having nominal amount for fibrinogen and thrombin (1700 mg and 300 mg respectively) relative to the hemostatic biologics-containing pad having additionally 400 mg PEG 3000. Analysis of the data indicates that presence of PEG3000 significantly improved tissue peel strength of the hemostatic biologics-containing pad.

Example 3

Leak Testing

The leak test was performed as follows. A test sample of the hemostatic biologics-containing pad was subjected to incubation in porcine plasma while under a compression weight for three minutes. The sample was then placed on a flat metal fixture with a 4.5 mm aperture, and a clear plastic top with a matching aperture was clamped over the hemostatic biologics-containing pad. The sample was then subjected to porcine plasma delivered as a hydraulic fluid through the aperture at a constant flow rate. Leaking was therefore the only failure mode allowed, and the peak pressures were recorded as outputs.

Figure 2:
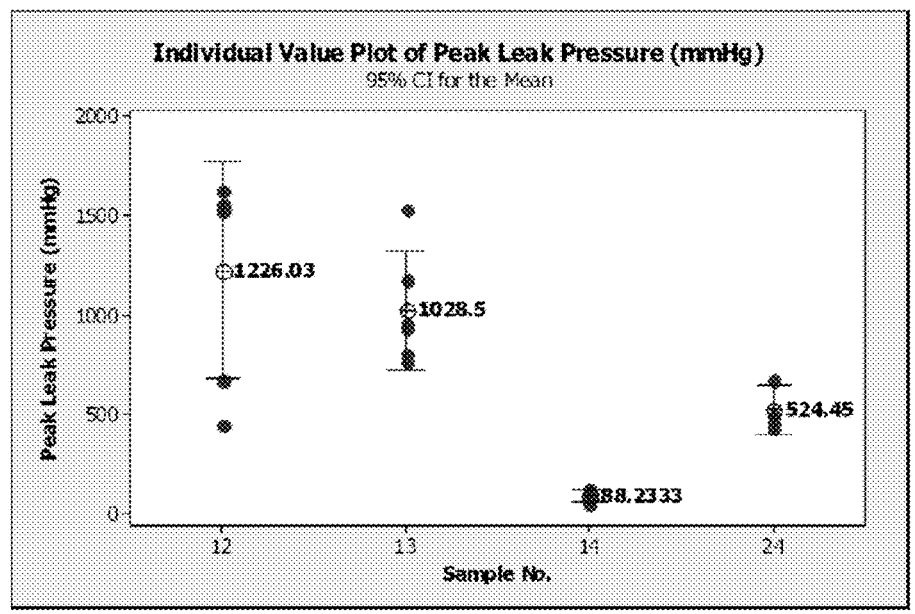
FIG. 2 shows leak test data for several tested systems

Referring now to Table 2 and to FIG. 2, the results of the leak test are presented for two different quantities of BAC2: 1.7 g and 1.27 g of fibrinogen-containing BAC-2 powder per 4×4" hemostatic biologics-containing pad sample; 0 and 400 mg of PEG3000; and 0 and 300 mg of CMC 30 k; all quantities are per 4"×4" hemostatic biologics-containing pad sample.

TABLE 2

Leak test results

| Pad sample No. | BAC2 (g) | Thrombin (mg) | PEG3000 (mg) | CMC 30k (mg) | Mean Peak Leak P (mmHg) |
|---|---|---|---|---|---|
| 14 (Nominal) | 1.700 | 300 | 0 | 0 | 88 ± 27 |
| 12 | 1.700 | 300 | 400 | 0 | 1226 ± 523 |
| 13 | 1.700 | 300 | 400 | 300 | 1029 ± 286 |
| 24 | 1.270 | 300 | 400 | 300 | 524 ± 119 |

Analysis of the data indicates that presence of PEG3000 significantly improves strength of the hemostatic biologics-containing pad in the leak test (Samples 12, 13, 24) relative to the hemostatic biologics-containing pad without the addition of PEG (sample 14). The average leak test pressure improvement ranges from about 6 times better to about 14 times better.

Example 4

Friability Testing

Figure 3:
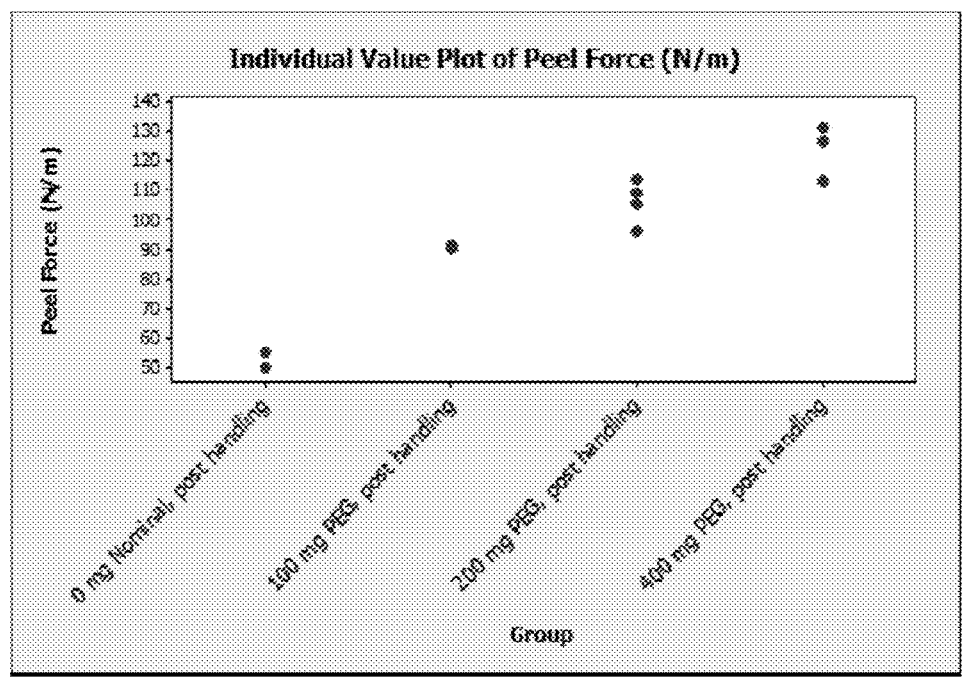
FIG. 3 shows the results of the friability testing for different concentrations of PEG3

Referring now to Table 3 and to FIG. 3, the results of the friability testing are presented for four different concentrations of PEG3000 (0, 100, 200, and 400 mg; all concentrations per 4"×4" hemostatic biologics-containing pad sample) after hemostatic biologics-containing pad handling.

The friability testing for powder weight loss after handling was performed as follows. A test sample of the hemostatic biologics-containing pad was subjected to extreme handling practices employed. The weight of the 4×4 inch hemostatic biologics-containing pad was first recorded. Then the hemostatic pad was held in one hand about three inches above the bench top, with the coated side facing down. The pad was cut using surgical scissors into roughly two 2×4 inch pieces. The piece not held was allowed to fall onto a surgical drape on the bench top. Then each of the two 2×4 inch pieces were held at 12 inches above the surgical drape on the bench top, and both were respectively dropped three times. The two pieces were weighed on the balance, and a mass balance was conducted to calculate the percent powder loss from the original 4×4 inch sample. Samples used contained varying amounts of PEG and contained no CMC. The results are shown in Table 3.

TABLE 3

Friability Test: Powder weight loss after handling

| Pad sample No. | BAC2 (g) | Thrombin (mg) | PEG3000 (mg) | Percent Powder Loss |
|---|---|---|---|---|
| 5 | 1.700 | 300 | 0 | 16.0 |
| 6 | 1.700 | 300 | 100 | 2.6 |
| 7 | 1.700 | 300 | 200 | 2.2 |
| 8 | 1.700 | 300 | 400 | 1.4 |

Analysis of the data of Table 3 indicates that presence of PEG3000 resulted in significantly reduced friability of the hemostatic biologics-containing pad in the friability test (Samples 6, 7, 8) relative to the hemostatic biologics-containing pad without the addition of PEG (sample 5), with the powder loss decreasing by a factor of about 11 at the highest content of PEG of 400 mg to about factor of 6 at the lowest PEG amount present corresponding to 100 mg of PEG.

Samples that were subjected to extreme handling practices as described above were then tissue peel tested as described in Example 2. This test demonstrated the synergistic effects of reduced friability and enhanced wetting and tissue peel strength for samples which contained PEG amounts of 100, 200 and 400 mg per 4×4" device relative to samples containing 0 mg of PEG. Tissue peel force was measured for test samples of hemostatic biologics-containing pads subjected to standardized extreme handling as described above, and the results are reflecting a synergistic combination of friability reduction and adhesion improvement. Analysis of the experimental results presented in FIG. 3 indicates that presence of PEG3000 significantly improved the peel force after the samples that were subjected to extreme handling. A positive PEG dose response was evidenced in the tissue peel results, with increasing PEG contents resulting in increasing tissue peel strengths, with a 2-2.5 factor improvement for samples containing 400 mg PEG relative to samples containing no PEG.

Example 5

Fibrin Gelation Test

A fibrin gelation test measuring time for a sample to clot a fibrinogen solution (tilt tube method) was performed as follows. Fibrinogen (ERL FIB3) was dissolved in 200 mM Tris buffered saline at a concentration of 10 mg/ml. A sample of an inventive hemostatic biologics-containing pad or a control hemostatic biologics-containing pad, measuring about 1 cm$^2$, was placed at the bottom of a 12×75 mm borosilicate glass tube. The sample was positioned with the coated side facing up in the tube. Then 2 ml of the 10 mg/ml fibrinogen solution was added to the tube, which was covered and then immediately placed tube rack in a 37° C. water bath. Every ten seconds the tube was manually inverted and then placed back in the rack within the water bath. Observations were made at every inversion, and the end point was the time when complete gel formation was observed, i.e. no obvious bulk fluid movement in the tube.

The results of the testing are as follows. For the control hemostatic biologics-containing pad sample containing no PEG and no CMC, the time for sample to clot a fibrinogen solution in two tests was 230 and 270 seconds. For the inventive Hemostatic biologics-containing pad containing 400 mg PEG3000 and 300 mg CMC, all concentrations per 4"×4" Hemostatic biologics-containing pad sample, the time for sample to clot a fibrinogen solution in two tests was 90 and 120 seconds.

The results indicate faster fibrinogen solution clotting and thus faster wetting/lesser hydrophobicity/better availability of thrombin in the hemostatic biologics-containing pads containing PEG and CMC.

Example 6

Water Ingress Study

A water ingress study was performed as follows. A hemostatic biologics-containing pad sample measuring about 1 cm$^2$ was subjected to a water droplet delivered onto its actively coated side by a syringe. The time for water droplet to wick into sample was then measured.

The results of the testing are as follows. For a nominal Hemostatic biologics-containing pad containing no PEG, the time for water droplet to wick into sample was observed to be on the order of minutes, i.e. more than about 1-2 minutes. For the inventive hemostatic biologics-containing pad containing 400 mg PEG3000 and 300 mg CMC, the time for water droplet to wick into sample was on the order of milliseconds.

The results indicate faster wetting and less hydrophobicity of the hemostatic biologics-containing pads containing PEG and CMC.

While the above examples demonstrate certain embodiments of the invention, they are not to be interpreted as limiting the scope of the invention, but rather as contributing to a complete description of the invention.

We claim:

1. A hemostatic pad comprising:
    a) a bioabsorbable scaffolding material;
    b) a thrombin powder particle,
    c) a fibrinogen powder particle, and
    d) a meltable binder powder that is a hydrophilic, biocompatible, and bioabsorbable material having a melting point from about 25° C. to about 100° C.,
  wherein said thrombin and fibrinogen powder particles are disposed on the bioabsorbable scaffolding material and the meltable binder powder bonds the thrombin powder particles and the fibrinogen powder particles to the bioabsorbable scaffolding material but does not coat or fully envelope the thrombin powder particles and/or the fibrinogen powder particles.

2. The hemostatic pad according to claim 1 wherein the meltable binder comprises a polyethylene glycol polymer having an average molecular weight from about 1500 to about 20,000 Daltons.

3. The hemostatic pad according to claim 1 wherein the meltable binder is composed substantially of polyethylene glycol polymer having an average molecular weight from about 2500 to about 8000 Daltons, more preferably from about 2500 to about 4000 Daltons.

4. The hemostatic pad according to claim 3 wherein average molecular weight of the polyethylene glycol polymer for the binder powder is about 3000 Daltons.

5. The hemostatic pad according to claim 2 wherein the binder particles have a number average particle size of about 45 microns.

6. The hemostatic pad according to claim 2 wherein the weight fraction of the thrombin powder is about 10-15%, the fibrinogen powder is about 55-85%, and the polyethylene glycol is 2-20%, each relative to total weight of the thrombin, fibrinogen and polyethylene glycol powders on the hemostatic pad.

7. The hemostatic pad according to claim 2 wherein the bioabsorbable scaffolding material is a woven or a non-woven synthetic or natural bioabsorbable material or combinations thereof.

8. The hemostatic pad according to claim 2 wherein the bioabsorbable scaffolding material is a bi-layer material comprising a layer of non-woven Polyglactin 910 fibers that has been needle punched into a layer of knitted oxidized regenerated cellulose, wherein said powders are disposed only on said layer of non-woven Polyglactin 910 fibers.

9. The hemostatic pad according to claim 2 wherein said thrombin powder particles and said fibrinogen powder particles are bonded to the bioabsorbable scaffolding material by elevating the temperature of the hemostatic pad to a point above the melting point of the polyethylene glycol polymer.

10. The hemostatic pad according to claim 2 wherein said hemostatic pad contains about 200-600 IU of thrombin per square inch of said hemostatic pad, as measured when applied, contains fibrinogen in the amount of about 20-80 mg per square inch of said hemostatic pad, as measured when applied, and the polyethylene glycol is present in the amount of about 6-25 mg per square inch of said hemostatic pad.

11. The hemostatic pad according to claim 2 further comprising carboxymethyl cellulose powder.

12. The hemostatic pad according to claim 11 wherein said carboxymethyl cellulose powder has a number average particle size of about 20 microns and wherein said carboxymethyl cellulose powder is present in an amount of about 15-20 mg per square inch of said hemostatic pad.

* * * * *